(12) United States Patent
Finkelstein

(10) Patent No.: US 7,674,923 B2
(45) Date of Patent: Mar. 9, 2010

(54) PROCESS FOR PREPARING FORMS OF ATORVASTATIN CALCIUM SUBSTANTIALLY FREE OF IMPURITIES

(75) Inventor: Nina Finkelstein, Herzliya (IS)

(73) Assignee: Teva Pharmaceutical Industries Ltd, Petah Tiqva (IL)

(*) Notice: Subject to any disclaimer, the term of this patent is extended or adjusted under 35 U.S.C. 154(b) by 366 days.

(21) Appl. No.: 11/236,647

(22) Filed: Sep. 28, 2005

(65) Prior Publication Data

US 2006/0142592 A1 Jun. 29, 2006

Related U.S. Application Data

(60) Provisional application No. 60/613,687, filed on Sep. 28, 2004.

(51) Int. Cl.
C07D 493/06 (2006.01)
(52) U.S. Cl. .................................................... 549/464
(58) Field of Classification Search ................. 549/464
See application file for complete search history.

(56) References Cited

U.S. PATENT DOCUMENTS

| | | | |
|---|---|---|---|
| 4,681,893 | A | 7/1987 | Roth |
| 5,273,995 | A | 12/1993 | Roth |
| 5,969,156 | A | 10/1999 | Briggs et al. |
| 6,121,461 | A | 9/2000 | McKenzie |
| 6,333,198 | B1 | 12/2001 | Edmeades et al. |
| 6,605,729 | B1 | 8/2003 | Bym et al. |
| 6,695,969 | B1 | 2/2004 | Grahek et al. |
| 2002/0115709 | A1 | 8/2002 | Aronhime et al. |
| 2002/0183378 | A1 | 12/2002 | Aronhime et al. |
| 2003/0114497 | A1 | 6/2003 | Alanai et al. |
| 2007/0208071 | A1 | 9/2007 | Grahek et al. |

FOREIGN PATENT DOCUMENTS

| | | |
|---|---|---|
| EP | 1 424 324 | 6/2004 |
| SI | 200400209 | 7/2004 |
| WO | WO 01/28999 | 4/2001 |
| WO | WO 01/36384 | 5/2001 |
| WO | WO 02/043732 | 6/2002 |
| WO | WO 03/011826 | 2/2003 |
| WO | WO 2004/050618 | 6/2004 |
| WO | WO 2006/000091 | 1/2006 |

OTHER PUBLICATIONS

Hurley et al. "Photodecomposition of CI-981, an HMG-CoA Reductase Inhibitor" *Tetrahedron*, vol. 49, No. 10, pp. 1979-1984, (1993).
Pedersen et al. "Randomised trial of cholesterol lowering in 4444 patients with coronary heart disease: the Scandinavian Simvastatin Survival Study (4S)" *The Lancet*, vol. 344, p. 1383-1389, (1994).
Goodman & Gilman's "The Pharmacological Basis of Therapeutics" $9^{th}$ Ed. (1996), pp. 879-881.
Snyder, et al., *Introduction To Modern Liquid Chromatography*, $2^{nd}$ Ed., 1979, pp. 549-572, John Wiley & Sons, Inc.
Strobel, et al., *Chemical Instrumentation: A Systematic Approach*, $3^{rd}$ Ed., 1989, pp. 391-393, 879-894, 922-925, 953.
Lipid Research Clinics Program, "The Lipid Research Clinics Coronary Primary Prevention Trial Results: I. Reduction In Incidence of Coronary Heart Disease", *J.A.M.A.*, 1984, 351-74, vol. 251, No. 3.***.
Third Party Observation dated Aug. 28, 2007 filed in EP counterpart application No. 0500195.9 ****.

*Primary Examiner*—Taofiq A Solola
(74) *Attorney, Agent, or Firm*—Kenyon & Kenyon LLP

(57) ABSTRACT

The preparation of atorvastatin calcium epoxide dihydroxy (AED) is described. AED can be used as a standard or marker in determining the amount of AED in a sample. AED can therefore be used as a tool in preparing atorvastatin calcium substantially free of AED.

1 Claim, 4 Drawing Sheets

VWD1 A, Wavelength =254 nm

Area Percent Report

Sorted By      : Signal
Multiplier     : 1.0000
Dilution       : 1.0000
Use Multiplier & Dilution Factor with ISIDs Signal 1: VUD1 A, Wavelength+254 nm

| Peak # | Retine [min] | Type | Width [min] | Area nAU *s | Height nAU | Area % |
|---|---|---|---|---|---|---|
| 1 | 27.202 | BB | 0.1567 | 6.19643 | 6.23776e-1 | 0.0858 |
| 1 | 30.872 | BV | 0.1709 | 17.34458 | 1.47264 | 0.2400 |
| 3 | 31.791 | VB | 0.1235 | 6949.49316 | 872.40076 | 96.1521 |
| 4 | 33.020 | BB | 0.1276 | 254.56876 | 31.01283 | 3.5222 |
| Totals: | | | | 7227.60493 | 905.51001 | |

PROCESS FOR PREPARING FORMS OF ATORVASTATIN CALCIUM SUBSTANTIALLY FREE OF IMPURITIES

This application claims the benefit of U.S. Provisional Patent Application Ser. No. 60/613,687 filed Sep. 28, 2004, which is incorporated herein by reference.

FIELD OF INVENTION

The present invention relates to atorvastatin calcium impurities and processes for preparing atorvastatin calcium substantially free of impurities.

BACKGROUND OF THE INVENTION (βR,δR)-2-(4-fluorophenyl)-β,δ-dihydroxy-5-(1-methylethyl)-3-phenyl-4-[(phenylamino)carbonyl]-1H-pyrrole-1-heptanoic acid ("atorvastatin") of formula (I)

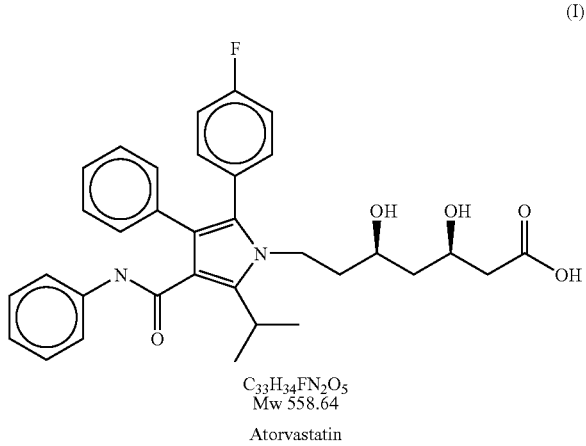

$C_{33}H_{34}FN_2O_5$
Mw 558.64

Atorvastatin is well known in the art, and described, inter alia, in U.S. Pat. Nos. 4,681,893, 5,273,995.

Atorvastatin calcium is a member of the class of drugs called statins. Statin drugs are said to be the most therapeutically effective drugs currently available for reducing low density lipoprotein (LDL) particle concentration in the blood stream of patients at risk for cardiovascular disease. A high level of LDL in the bloodstream has been linked to the formation of coronary lesions which obstruct the flow of blood and can rupture and promote thrombosis. Goodman and Gilman's *The Pharmacological Basis of Therapeutics* 879 (9th ed. 1996). Reducing plasma LDL levels has been shown to reduce the risk of clinical events in patients with cardiovascular disease and patients who are free of cardiovascular disease but who have hypercholesterolemia. Scandinavian Simvastatin Survival Study Group, 1994; Lipid Research Clinics Program, 1984a, 1984b.

Atorvastatin calcium is marketed under the name LIPITOR® by Pfizer, Inc. Atorvastatin was first claimed in U.S. Pat. No. 4,681,893. The hemi-calcium salt of atorvastatin is disclosed in U.S. Pat. No. 5,273,995. Distinct crystalline forms are disclosed in several patents and patent applications. Crystalline Forms I, II, III and IV of atorvastatin calcium are the subjects of U.S. Pat. Nos. 5,959,156 and 6,121,461 assigned to Warner-Lambert and crystalline atorvastatin calcium Forms V and VIII are disclosed in commonly-owned published application nos. WO 01/36384 and US 2002/0183378, both of which are herein incorporated by reference.

Like any synthetic compound, atorvastatin hemi-calcium salts can contain extraneous compounds or impurities that can come from many sources. They can be unreacted starting materials, by-products of the reaction, products of side reactions, or degradation products. Impurities in atorvastatin hemi-calcium salts or any active pharmaceutical ingredient (API) are undesirable and, in extreme cases, might even be harmful to a patient being treated with a dosage form containing the API.

It is also known in the art that impurities in an API may arise from degradation of the API itself, which is related to the stability of the pure API during storage, and the manufacturing process, including the chemical synthesis. Process impurities include unreacted starting materials, chemical derivatives of impurities contained in starting materials, synthetic by-products, and degradation products.

In addition to stability, which is a factor in the shelf life of the API, the purity of the API produced in the commercial manufacturing process is clearly a necessary condition for commercialization. Impurities introduced during commercial manufacturing processes must be limited to very small amounts, and are preferably substantially absent. For example, the ICH Q7A guidance for API manufacturers requires that process impurities be maintained below set limits by specifying the quality of raw materials, controlling process parameters, such as temperature, pressure, time, and stoichiometric ratios, and including purification steps, such as crystallization, distillation, and liquid-liquid extraction, in the manufacturing process.

The product mixture of a chemical reaction is rarely a single compound with sufficient purity to comply with pharmaceutical standards. Side products and by-products of the reaction and adjunct reagents used in the reaction will, in most cases, also be present in the product mixture. At certain stages during processing of an API, such as atorvastatin calcium, it must be analyzed for purity, typically, by HPLC or TLC analysis, to determine if it is suitable for continued processing and, ultimately, for use in a pharmaceutical product. The API need not be absolutely pure, as absolute purity is a theoretical ideal that is typically unattainable. Rather, purity standards are set with the intention of ensuring that an API is as free of impurities as possible, and, thus, is as safe as possible for clinical use. As discussed above, in the United States, the Food and Drug Administration guidelines recommend that the amounts of some impurities be limited to less than 0.1 percent.

Generally, side products, by-products, and adjunct reagents (collectively "impurities") are identified spectroscopically and/or with another physical method, and then associated with a peak position, such as that in a chromatogram, or a spot on a TLC plate. (Strobel p. 953, Strobel, H. A.; Heineman, W. R., Chemical Instrumentation: A Systematic Approach, 3rd dd. (Wiley & Sons: New York 1989)). Thereafter, the impurity can be identified, e.g., by its relative position in the chromatogram, where the position in a chromatogram is conventionally measured in minutes between injection of the sample on the column and elution of the particular component through the detector. The relative position in the chromatogram is known as the "retention time."

The retention time can vary about a mean value based upon the condition of the instrumentation, as well as many other factors. To mitigate the effects such variations have upon accurate identification of an impurity, practitioners use the "relative retention time" ("RRT") to identify impurities. (Strobel p. 922). The RRT of an impurity is its retention time divided by the retention time of a reference marker. It may be advantageous to select a compound other than the API that is added to, or present in, the mixture in an amount sufficiently large to be detectable and sufficiently low as not to saturate the column, and to use that compound as the reference marker for determination of the RRT.

Those skilled in the art of drug manufacturing research and development understand that a compound in a relatively pure state can be used as a "reference standard." A reference standard is similar to a reference marker, which is used for qualitative analysis only, but is used to quantify the amount of the compound of the reference standard in an unknown mixture, as well. A reference standard is an "external standard," when a solution of a known concentration of the reference standard and an unknown mixture are analyzed using the same technique. (Strobel p. 924, Snyder p. 549, Snyder, L. R.; Kirkland, J. J. Introduction to Modern Liquid Chromatography, 2nd ed. (John Wiley & Sons: New York 1979)). The amount of the compound in the mixture can be determined by comparing the magnitude of the detector response. See also U.S. Pat. No. 6,333,198, incorporated herein by reference.

The reference standard can also be used to quantify the amount of another compound in the mixture if a "response factor," which compensates for differences in the sensitivity of the detector to the two compounds, has been predetermined. (Strobel p. 894). For this purpose, the reference standard is added directly to the mixture, and is known as an "internal standard." (Strobel p. 925, Snyder p. 552).

The reference standard can serve as an internal standard when, without the deliberate addition of the reference standard, an unknown mixture contains a detectable amount of the reference standard compound using the technique known as "standard addition."

In a the "standard addition technique", at least two samples are prepared by adding known and differing amounts of the internal standard. (Strobel pp. 391-393, Snyder pp. 571, 572). The proportion of the detector response due to the reference standard present in the mixture without the addition can be determined by plotting the detector response against the amount of the reference standard added to each of the samples, and extrapolating the plot to zero concentration of the reference standard. (See, e.g., Strobel, FIG. 11.4 p. 392). The response of a detector in HPLC (e.g. UV detectors or refractive index detectors) can be and typically is different for each compound eluting from the HPLC column. Response factors, as known, account for this difference in the response signal of the detector to different compounds eluting from the column.

As is known by those skilled in the art, the management of process impurities is greatly enhanced by understanding their chemical structures and synthetic pathways, and by identifying the parameters that influence the amount of impurities in the final product.

Like any synthetic compound, atorvastatin calcium can contain extraneous compounds or impurities that can come from many sources. They can be unreacted starting materials, by-products of the reaction, products of side reactions, or degradation products.

In this application the reference marker is the impurity N-formyl atorvastatin calcium in the API. Detection or quantification of the reference marker serves to establish the level of purity of the API. Use of a compound as a reference marker requires recourse to a sample of substantially pure compound.

Thus, there is a need in the art for a method for determining the level of impurities in atorvastatin calcium samples.

SUMMARY OF THE INVENTION

In one aspect the present invention provides the isolated atorvastatin calcium derivative—atorvastatin calcium epoxy dihydroxy (AED), having the formula:

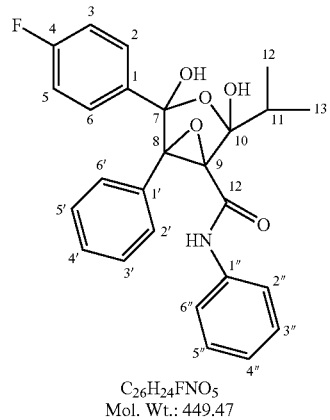

$C_{26}H_{24}FNO_5$
Mol. Wt.: 449.47

The isolated AED of the present invention may be characterized by data selected from: $^1HNMR$ spectrum having hydrogen chemical shifts at about 1.20, 1.21, 2.37, 4.310, 6.032, 7.00, 7.06-7.29, 7.30, 7.39, 7.41, 7.56 ppm; a $^{13}CNMR$ spectrum having carbon chemical shifts at about 16.97, 34.66, 103.49, 106.66, 114.72, 120.59, 125.79, 128.21, 128.55, 128.74, 129.06, 129.57, 132.38, 132.51, 135.15, 161.61, 163.23 ppm; an MS (ESI$^+$) spectrum having peaks at about having: m/z=472(MNa)$^+$, 454 (MNa—H$_2$O)$^+$, 432 (MH—H$_2$O)$^+$; 344 (FPhCOC(Ph)=C—CONHPh)$^+$ by retention time of about 32 min in HPLC analysis, such as the one described herein below, and by a relative retention time of about 1.88.

In another aspect, the present invention further provides a process for preparing AED comprising the steps of:
(a) combining atorvastatin calcium salt and a polar organic solvent or mixtures thereof with water, with methylene blue, to obtain a solution;
(b) irradiating the obtained solution for about 2 to about 10 hours;
(c) recovering AED.

Preferably, the irradiation of the solution of step (a) is performed in the presence of oxygen or air, in order to produce a photooxidation reaction. Therefore, the reaction is conducted, preferably, in an open vessel.

Preferably, the light source for irradiation is selected from the group consisting of a tungsten lamp, a UV lamp or sun light. More preferably, the light source for irradiation is a tungsten lamp. Moreover, when using a tungsten lamp as a light source, the yield is increased.

In yet another aspect, the present invention also provides a method for determining the level of AED in atorvastatin calcium comprising
(a) measuring by HPLC the area under a peak corresponding to AED in a reference standard comprising a known amount of AED;
(b) measuring by HPLC the area under a peak corresponding to AED in a sample comprising atorvastatin calcium and AED;
(c) determining the amount of AED in the sample by comparing the area of step (a) to the area of step (b).

Unless otherwise specified, "atorvastatin calcium" may be either crude atorvastatin calcium or any form of atorvastatin, including, for example, crystalline Forms I, II, IV, V, VI, VII, VIII, IX, X, XI, XII and amorphous.

Preferably, the HPLC methodology used in the above method (for the use of AED as reference standard) includes the steps (a) combining an atorvastatin calcium sample with a mixture of acetonitrile:tetrahydrofuran:water in a ratio of about 60:5:35, to obtain a solution;
(b) injecting the solution of step (a) into a 250×4.6 mm KR 100 5C-18 (or similar) column;
(c) eluting the sample from the column at about 50 min using a mixture of acetonitrile:tetrahydrofuran:buffer (31:9:60) and acetonitrile:buffer mix (75:25) as an eluent, and
(d) measuring the AED content in the relevant sample with a UV detector (preferably at a 254 nm wavelength).

In one aspect, the present invention provides an HPLC method for assaying atorvastatin calcium comprising the steps
(a) combining an atorvastatin calcium sample with a mixture of acetonitrile:tetrahydrofuran:water in a ratio of about 60:5:35, to obtain a solution;
(b) injecting the solution of step (a) into a 250×4.6 mm KR 100 5C-18 (or similar) column;
(c) eluting the sample from the column at about 50 min using a mixture of acetonitrile:tetrahydrofuran:buffer (31:9:60) and acetonitrile:buffer mix (75:25) as an eluent, and
(d) measuring the AED content in the relevant sample with a UV detector (preferably at a 254 nm wavelength).

Preferably, the buffer contains an aqueous solution of $NH_4H_2PO_4$ in a concentration of about 0.05M having a pH of about 5, and ammonium hydroxide. Preferably, the ratio of the aqueous solution of $NH_4H_2PO_4$ and ammonium hydroxide is of about 1 to 4, respectively.

Preferably, the buffer mix contains the above buffer and tetrahydrofuran. Preferably, the ratio of the above buffer and tetrahydrofuran is of about 1 to 6.67, respectively.

In another aspect, the present invention provides a process for preparing a form of atorvastatin calcium comprising less than about 0.10 w/w of, AED, by HPLC comprising the steps of
(a) obtaining one or more samples of one or more atorvastatin calcium batches;
(b) measuring the level of AED in each of the samples of (a);
(c) selecting the atorvastatin calcium batch that comprises a level of AED of less than about 0.10 w/w by HPLC, based on the measurement or measurements conducted in step (b); and
(d) using the batch selected in step (c) to prepare said any form of atorvastatin calcium.

Preferably, the atorvastatin calcium sample of step (a) comprises a sufficiently low level of AED. More preferably, the atorvastatin calcium sample of step (a) contains less than about 0.05 w/w by HPLC of AED.

Preferably, said any form of atorvastatin calcium refers to but is not limited to forms I, II, IV, V, VI, VII, VIII, IX, X, XI, XII and amorphous.

When the atorvastatin calcium sample of step (a) contains more than about 0.10 w/w by HPLC of AED, according to the measurement in step (b), the sample may be purified, prior to performing step (c).

Preferably, the atorvastatin calcium sample of step (a) obtained after purification, contains less than about 0.10 w/w by HPLC of AED, more preferably, of less than about 0.05 w/w by HPLC.

In yet another aspect, the present invention provides a method for reducing the level of AED in atorvastatin calcium sample by dissolving a selected form of atorvastatin calcium in an organic solvent, water or mixtures thereof, and crystallizing to obtain atorvastatin calcium having a reduced level of AED.

Preferably, the atorvastatin calcium sample obtained after purification contains less than about 0.10 w/w by HPLC of AED, more preferably, of less than about 0.05 w/w by HPLC.

Preferably, the selected form of atorvastatin calcium may be any form of atorvastatin, such as but not limited to form I, II, IV, V, VI, VII, VIII, IX, X, XI, XII and amorphous.

Preferably, when the selected form of atorvastatin calcium is the amorphous form, the crystallization is performed from either a mixture of ester and $C_{5-10}$ cyclic or aliphatic hydrocarbon, from a polar aprotic organic solvent or from a mixture of a $C_{6-10}$ aromatic hydrocarbon and a polar organic solvent, to give atorvastatin calcium amorphous form. Preferably, the ester is ethylacetate. A preferred $C_{5-10}$ cyclic or aliphatic hydrocarbon is hexane. Preferably, the polar organic solvent is either a ketone or a nitrile. A preferred ketone is acetone. A preferred nitrile is acetonitrile. Preferably, the $C_{6-10}$ aromatic hydrocarbon is toluene. A preferred polar organic solvent is tetrahydrofuran.

Preferably, when the selected form of atorvastatin calcium is form I, the crystallization is performed from a mixture of water miscible organic solvent and water, to give atorvastatin calcium form I. Preferably, the polar organic solvent is a mixture of $C_{1-4}$ alcohol and an ether. Preferably, the $C_{1-4}$ alcohol is methanol. A preferred ether is methyltertbutylether.

Preferably, when the selected form of atorvastatin calcium is form II, the crystallization is performed from a mixture of water miscible organic solvent and water, to give atorvastatin calcium form II. Preferably, the water miscible organic solvent is a $C_{1-4}$ alcohol. Preferably, the $C_{1-4}$ alcohol is methanol.

Preferably, when the selected form of atorvastatin calcium is form IV, the crystallization is performed from a water miscible organic solvent, water and mixtures thereof, to give atorvastatin calcium form IV. Preferably, the water miscible organic solvent is a $C_{1-4}$ alcohol. Preferably, the $C_{1-4}$ alcohol is methanol, ethanol or 1-butanol. Preferably, when a mixture of a water miscible organic solvent and water is used, the water miscible organic solvent is ethanol.

Preferably, when the selected form of atorvastatin calcium is form V, the crystallization is performed from a mixture of water miscible organic solvent and water, to give atorvastatin calcium form V. Preferably, the water miscible organic solvent is a $C_{1-4}$ alcohol. Preferably, the $C_{1-4}$ alcohol is ethanol.

Preferably, when the selected form of atorvastatin calcium is form VI, the crystallization is performed from a mixture of polar aprotic organic solvent and water, to give atorvastatin calcium form VI. Preferably, the polar aprotic organic solvent is a ketone. Preferably, the ketone is acetone.

Preferably, when the selected form of atorvastatin calcium is form VII, the crystallization is performed from a $C_{1-4}$ alcohol, to give atorvastatin calcium form VII. Preferably, the $C_{1-4}$ alcohol is ethanol.

Preferably, when the selected form of atorvastatin calcium is form VIII, the crystallization is performed from a water miscible organic solvent, water and mixtures thereof, to give atorvastatin calcium form VIII. Preferably, the water miscible organic solvent is a $C_{1-4}$ alcohol. Preferably, the $C_{1-4}$ alcohol is ethanol, methanol, 1-butanol or iso-propanol.

Preferably, when the selected form of atorvastatin calcium is form IX, the crystallization is performed from a water miscible organic solvent, a $C_{5-10}$ aliphatic hydrocarbon, water and mixtures thereof, to give atorvastatin calcium form IX. Preferably, the water miscible organic solvent is a $C_{1-4}$ alcohol. Preferably, the $C_{1-4}$ alcohol is ethanol, 1-butanol or iso-propanol. Preferably, the $C_{5-10}$ aliphatic hydrocarbon is hexane.

Preferably, when the selected form of atorvastatin calcium is form X, the crystallization is performed from a mixture of a water miscible organic solvent and water, to give atorvastatin calcium form X. Preferably, the water miscible organic solvent is a $C_{1-4}$ alcohol. Preferably, the $C_{1-4}$ alcohol is ethanol.

Preferably, when the selected form of atorvastatin calcium is form XI, the crystallization is performed from a polar aprotic organic solvent or from a water miscible organic solvent, to give atorvastatin calcium form XI. Preferably, the polar aprotic organic solvent is a ketone. Preferably, the water miscible organic solvent is a $C_{1-4}$ alcohol. Preferably, the ketone is methylethylketone. A preferred $C_{1-4}$ alcohol is isopropanol.

Preferably, when the selected form of atorvastatin calcium is form XII, the crystallization is performed from a mixture of a water miscible organic solvent and water, to give atorvastatin calcium form XII. Preferably, the water miscible organic solvent is a $C_{1-4}$ alcohol. A preferred $C_{1-4}$ alcohol is ethanol.

DETAILED DESCRIPTION OF THE INVENTION

Figure 1:
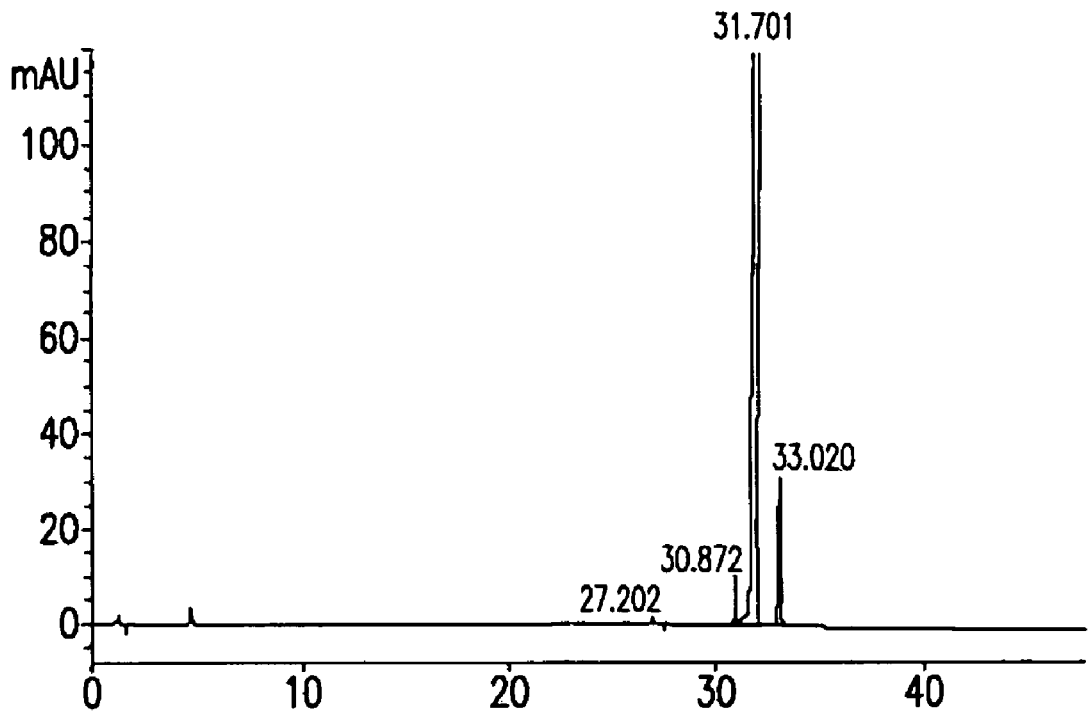
FIG. 1: HPLC chromatogram of AED.
Figure 2:
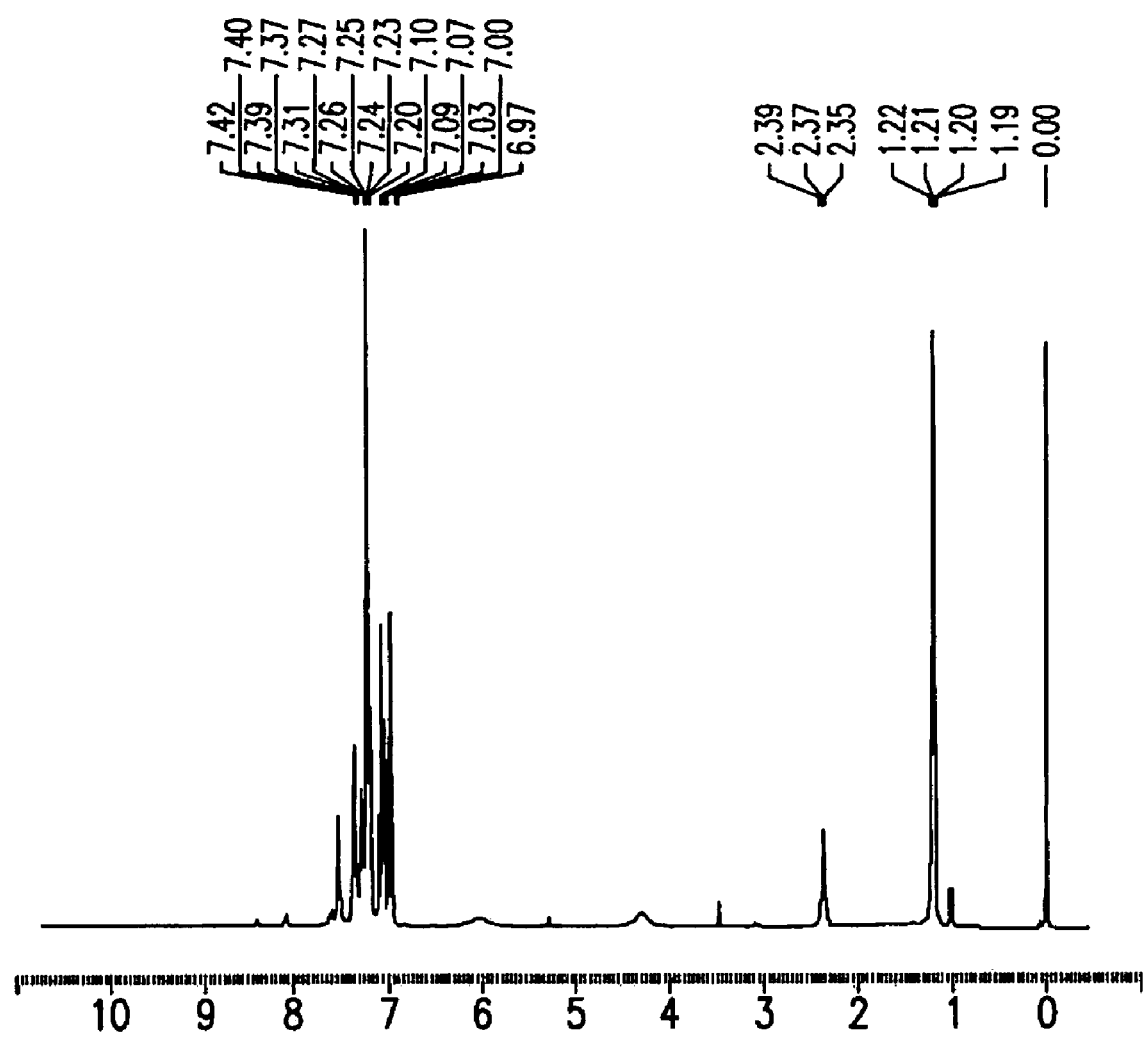
FIG. 2: $^1$HNMR spectrum of AED.
Figure 3:
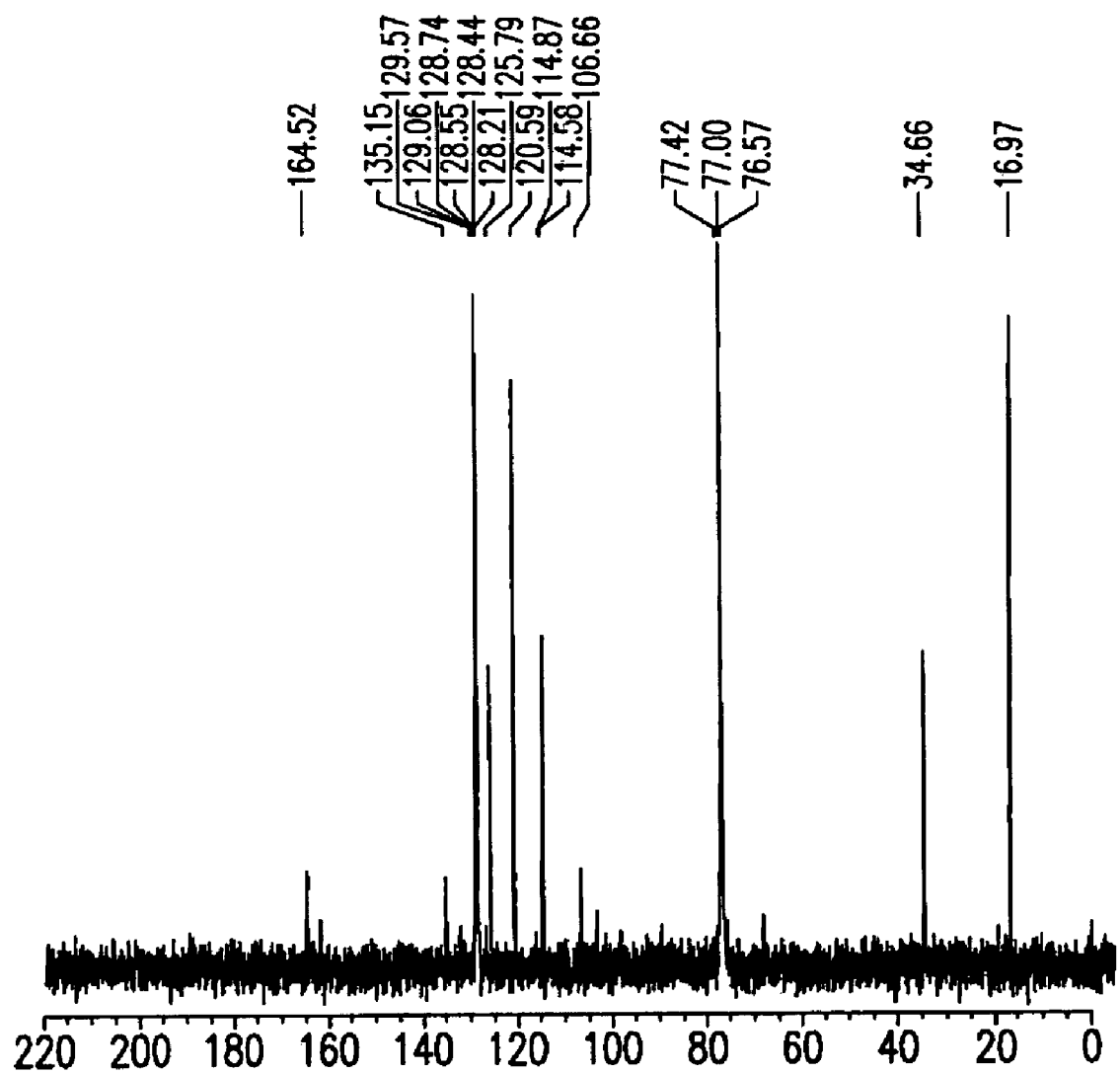
FIG. 3: $^{13}$CNMR spectrum of AED.
Figure 4:
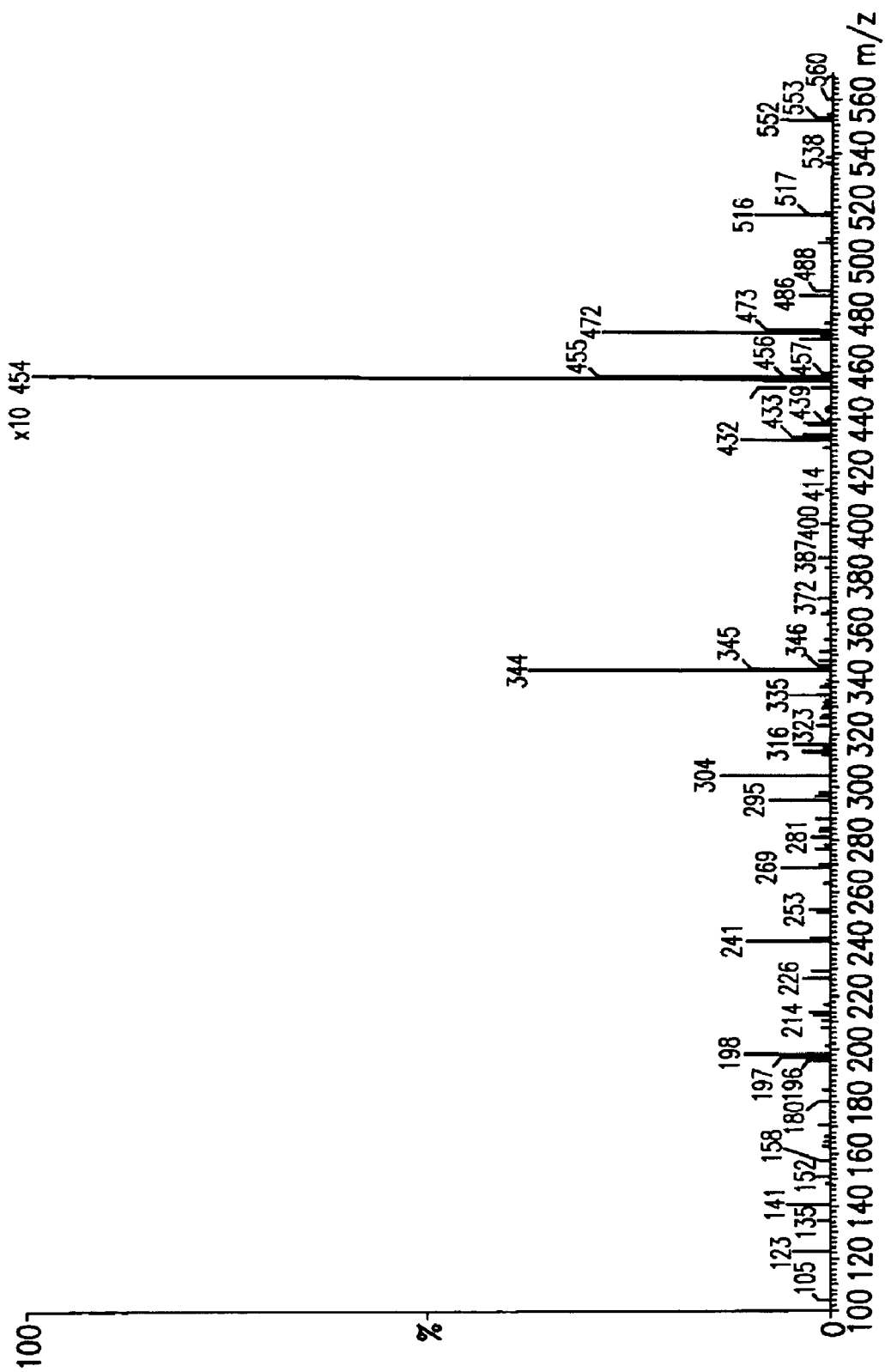
FIG. 4: MS spectrum of AED.

The present invention provides the isolated atorvastatin calcium derivative—atorvastatin calcium epoxy dihydroxy (AED), having the formula:

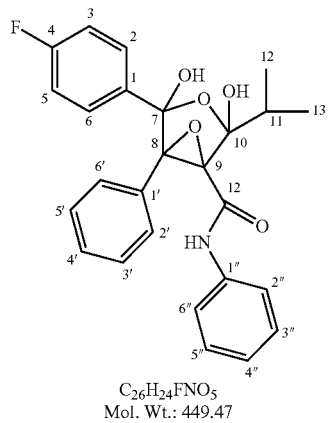

$C_{26}H_{24}FNO_5$
Mol. Wt.: 449.47

The isolated AED of the present invention may be characterized by data selected from: $^1$HNMR spectrum having hydrogen chemical shifts at about 1.20, 1.21, 2.37, 4.310, 6.032, 7.00, 7.06-7.29, 7.30, 7.39, 7.41, 7.56 ppm; a $^{13}$CNMR spectrum having carbon chemical shifts at about 16.97, 34.66, 103.49, 106.66, 114.72, 120.59, 125.79, 128.21, 128.55, 128.74, 129.06, 129.57, 132.38, 132.51, 135.15, 161.61, 163.23 ppm; an MS (ESI$^+$) spectrum having peaks at about having: m/z=472(MNa)$^+$, 454 (MNa—H$_2$O)$^+$, 432 (MH—H$_2$O)$^+$; 344 (FPhCOC(Ph)=C—CONHPh)$^+$ by retention time of about 32 min in HPLC analysis, such as the one described herein below, and by a relative retention time of about 1.88.

The present invention further provides a process for preparing AED comprising the steps of:
(a) combining atorvastatin calcium salt and a polar organic solvent or mixtures thereof with water, with methylene blue, to obtain a solution;
(b) irradiating the obtained solution for about 2 to about 10 hours;
(c) recovering AED.

Preferably, the polar organic solvent is selected from the group consisting of $C_{1-4}$ alcohol and nitrile. Preferably, the $C_{1-4}$ alcohol is either methanol or ethanol. A preferred nitrile is acetonitrile. Preferably, a mixture of acetonitrile and water is used in step (a).

Preferably, the irradiation of the solution of step (a) is performed in the presence of oxygen or air, in order to produce a photooxidation reaction. Therefore, the reaction is conducted, preferably, in an open vessel.

Preferably, the light source for irradiation is selected from the group consisting of a tungsten lamp, a UV lamp or sun light. More preferably, the light source for irradiation is a tungsten lamp. Moreover, when using a tungsten lamp as a light source, the yield is increased.

Preferably, the solution of step (a) is irradiated for about 2 hours.

Preferably, the crude AED may recovered by evaporating the polar organic solvent or mixtures thereof with water, more preferably, under vacuum, followed by filtration and drying to obtain a precipitate, crude AED.

The recovered crude AED may be purified by a process of chromatography on a silica-gel column with an eluent of water immiscible polar organic solvent or a mixture of a polar organic solvent and a $C_{5-8}$ aliphatic hydrocarbon. Preferably, the water immiscible polar organic solvent is dichloromethane. A preferred polar organic solvent is ethyl acetate.

Preferably, AED may be further purified by a process of precipitation from a water immiscible polar organic solvent or from a mixture of a polar organic solvent and a $C_{5-10}$ aliphatic hydrocarbon. Preferably, the water immiscible polar organic solvent is dichloromethane. A preferred polar organic solvent is ethyl acetate. Preferably, the $C_{5-10}$ aliphatic hydrocarbon is hexane.

The present invention also provides a method for determining the level of AED in atorvastatin calcium comprising
(a) measuring by HPLC the area under a peak corresponding to AED in a reference standard comprising a known amount of AED;
(b) measuring by HPLC the area under a peak corresponding to AED in a sample comprising atorvastatin calcium and AED;
(c) determining the amount of AED in the sample by comparing the area of step (a) to the area of step (b).

Unless otherwise specified, "atorvastatin calcium" may be either crude atorvastatin calcium or any form of atorvastatin, including, for example, crystalline Forms I, II, IV, V, VI, VII, VIII, IX, X, XI, XII and amorphous.

Preferably, the HPLC methodology used in the above method (for the use of AED as reference standard) includes the steps
(a) combining an atorvastatin calcium sample with a mixture of acetonitrile:tetrahydrofuran:water in a ratio of about 60:5:35, to obtain a solution;
(b) injecting the solution of step (a) into a 250×4.6 mm KR 100 5C-18 (or similar) column;
(c) eluting the sample from the column at about 50 min using a mixture of acetonitrile:tetrahydrofuran:buffer (31:9:60) and acetonitrile:buffer mix (75:25) as an eluent, and
(d) measuring the AED content in the relevant sample with a UV detector (preferably at a 254 nm wavelength).

The present invention further provides an HPLC method for assaying atorvastatin calcium comprising the steps
(a) combining an atorvastatin calcium sample with a mixture of acetonitrile:tetrahydrofuran:water in a ratio of about 60:5:35, to obtain a solution;

(b) injecting the solution of step (a) into a 250×4.6 mm KR 100 5C-18 (or similar) column;

(c) eluting the sample from the column at about 50 min using a mixture of acetonitrile:tetrahydrofuran:buffer (31:9:60) and acetonitrile:buffer mix (75:25) as an eluent, and (d) measuring the AED content in the relevant sample with a UV detector (preferably at a 254 nm wavelength).

Preferably, the buffer contains an aqueous solution of $NH_4H_2PO_4$ in a concentration of about 0.05M having a pH of about 5, and ammonium hydroxide. Preferably, the ratio of the aqueous solution of $NH_4H_2PO_4$ and ammonium hydroxide is of about 1 to 4, respectively.

Preferably, the buffer mix contains the above buffer and tetrahydrofuran. Preferably, the ratio of the above buffer and tetrahydrofuran is of about 1 to 6.67, respectively.

The present invention provides a process for preparing a form of atorvastatin calcium comprising less than about 0.10 w/w of, AED, by HPLC comprising the steps of (a) obtaining one or more samples of one or more atorvastatin calcium batches;

(b) measuring the level of AED in each of the samples of (a);

(c) selecting the atorvastatin calcium batch that comprises a level of AED of less than about 0.10 w/w by HPLC, based on the measurement or measurements conducted in step (b); and (d) using the batch selected in step (c) to prepare said any form of atorvastatin calcium.

Preferably, the atorvastatin calcium sample of step (a) comprises a sufficiently low level of AED. More preferably, the atorvastatin calcium sample of step (a) contains less than about 0.05 w/w by HPLC of AED.

Preferably, said any form of atorvastatin calcium refers to but is not limited to forms I, II, IV, V, VI, VII, VIII, IX, X, XI, XII and amorphous.

When the atorvastatin calcium sample of step (a) contains more than about 0.10 w/w by HPLC of AED, according to the measurement in step (b), the sample may be purified, prior to performing step (c).

Preferably, the atorvastatin calcium sample of step (a) obtained after purification, contains less than about 0.10 w/w by HPLC of AED, more preferably, of less than about 0.05 w/w by HPLC.

The purification may be performed by crystallization from an organic solvent, water, or mixtures thereof.

The present invention also provides a method for reducing the level of AED in atorvastatin calcium sample by dissolving a selected form of atorvastatin calcium in an organic solvent, water or mixtures thereof, and crystallizing to obtain atorvastatin calcium having a reduced level of AED.

Preferably, the atorvastatin calcium sample obtained after purification contains less than about 0.10 w/w by HPLC of AED, more preferably, of less than about 0.05 w/w by HPLC.

Preferably, the selected form of atorvastatin calcium may be any form of atorvastatin, such as but not limited to form I, II, IV, V, VI, VII, VIII, IX, X, XI, XII and amorphous.

Preferably, when the selected form of atorvastatin calcium is the amorphous form, the crystallization is performed from either a mixture of ester and $C_{5-10}$ cyclic or aliphatic hydrocarbon, from a polar aprotic organic solvent or from a mixture of a $C_{6-10}$ aromatic hydrocarbon and a polar organic solvent, to give atorvastatin calcium amorphous form. Preferably, the ester is ethylacetate. A preferred $C_{5-10}$ cyclic or aliphatic hydrocarbon is hexane. Preferably, the polar organic solvent is either a ketone or a nitrile. A preferred ketone is acetone. A preferred nitrile is acetonitrile. Preferably, the $C_{6-10}$ aromatic hydrocarbon is toluene. A preferred polar organic solvent is tetrahydrofuran.

Preferably, when the selected form of atorvastatin calcium is form I, the crystallization is performed from a mixture of water miscible organic solvent and water, to give atorvastatin calcium form I. Preferably, the polar organic solvent is a mixture of $C_{1-4}$ alcohol and an ether. Preferably, the $C_{1-4}$ alcohol is methanol. A preferred ether is methyltertbutylether.

Preferably, when the selected form of atorvastatin calcium is form II, the crystallization is performed from a mixture of water miscible organic solvent and water, to give atorvastatin calcium form II. Preferably, the water miscible organic solvent is a $C_{1-4}$ alcohol. Preferably, the $C_{1-4}$ alcohol is methanol.

Preferably, when the selected form of atorvastatin calcium is form IV, the crystallization is performed from a water miscible organic solvent, water and mixtures thereof, to give atorvastatin calcium form IV. Preferably, the water miscible organic solvent is a $C_{1-4}$ alcohol. Preferably, the $C_{1-4}$ alcohol is methanol, ethanol or 1-butanol. Preferably, when a mixture of a water miscible organic solvent and water is used, the water miscible organic solvent is ethanol.

Preferably, when the selected form of atorvastatin calcium is form V, the crystallization is performed from a mixture of water miscible organic solvent and water, to give atorvastatin calcium form V. Preferably, the water miscible organic solvent is a $C_{1-4}$ alcohol. Preferably, the $C_{1-4}$ alcohol is ethanol.

Preferably, when the selected form of atorvastatin calcium is form VI, the crystallization is performed from a mixture of polar aprotic organic solvent and water, to give atorvastatin calcium form VI. Preferably, the polar aprotic organic solvent is a ketone. Preferably, the ketone is acetone.

Preferably, when the selected form of atorvastatin calcium is form VII, the crystallization is performed from a $C_{1-4}$ alcohol, to give atorvastatin calcium form VII. Preferably, the $C_{1-4}$ alcohol is ethanol.

Preferably, when the selected form of atorvastatin calcium is form VIII, the crystallization is performed from a water miscible organic solvent, water and mixtures thereof, to give atorvastatin calcium form VIII. Preferably, the water miscible organic solvent is a $C_{1-4}$ alcohol. Preferably, the $C_{1-4}$ alcohol is ethanol, methanol, 1-butanol or iso-propanol.

Preferably, when the selected form of atorvastatin calcium is form IX, the crystallization is performed from a water miscible organic solvent, a $C_{5-10}$ aliphatic hydrocarbon, water and mixtures thereof, to give atorvastatin calcium form IX. Preferably, the water miscible organic solvent is a $C_{1-4}$ alcohol. Preferably, the $C_{1-4}$ alcohol is ethanol, 1-butanol or iso-propanol. Preferably, the $C_{5-10}$ aliphatic hydrocarbon is hexane.

Preferably, when the selected form of atorvastatin calcium is form X, the crystallization is performed from a mixture of a water miscible organic solvent and water, to give atorvastatin calcium form X. Preferably, the water miscible organic solvent is a $C_{1-4}$ alcohol. Preferably, the $C_{1-4}$ alcohol is ethanol.

Preferably, when the selected form of atorvastatin calcium is form XI, the crystallization is performed from a polar aprotic organic solvent or from a water miscible organic solvent, to give atorvastatin calcium form XI. Preferably, the polar aprotic organic solvent is a ketone. Preferably, the water miscible organic solvent is a $C_{1-4}$ alcohol. Preferably, the ketone is methylethylketone. A preferred $C_{1-4}$ alcohol is iso-propanol.

Preferably, when the selected form of atorvastatin calcium is form XII, the crystallization is performed from a mixture of a water miscible organic solvent and water, to give atorvastatin calcium form XII. Preferably, the water miscible organic solvent is a $C_{1-4}$ alcohol. A preferred $C_{1-4}$ alcohol is ethanol.

Optionally, the crystallization process may be repeated as necessary to obtain the desired atorvastatin calcium purity.

In order to preserve the purity level of atorvastatin calcium, the sample is maintained at a temperature of less than about 8° C., preferably the sample is maintained at a temperature of less than about 4° C.

Having described the invention with reference to certain preferred embodiments, other embodiments will become apparent to one skilled in the art from consideration of the specification. The invention is further defined by reference to the following examples describing in detail the preparation of the composition and methods of use of the invention. It will be apparent to those skilled in the art that many modifications, both to materials and methods, may be practiced without departing from the scope of the invention.

EXAMPLES

General

NMR analysis was done on Bruker DPX (300 MHz for $^1$HNMR, 150 MHz for $^{13}$CNMR), solvent CDCl$_3$.

Mass spectrometry was done on Micromass Q-TOS by method ESI$^+$

| HPLC method | |
|---|---|
| Column & Packing: | Kromasil KR 100 5C-18 250 × 4.6 mm is suitable. |
| Eluent A: | Acetonitrile:Tetrahydrofuran:Buffer 31:9:60 |
| Eluent B: | Acetonitrile:Buffer Mix 75:25 |
| Buffer solution: | 0.05M aqueous NH$_4$H$_2$PO$_4$ adjusted to pH 5.0 with NH$_4$OH (diluted about 1:4) |
| Buffer Mix: | A mixture of buffer solution and THE 60 volumes buffer and 9 volumes THF |
| Gradient conditions: | Time (minutes) | % Eluent A | % Eluent B | Flow rate |
| | 0 | 100 | 0 | 1.8 |
| | 20 | 100 | 0 | 1.8 |
| | 30 | 45 | 55 | 2.0 |
| | 40 | 0 | 100 | 2.5 |
| | 50 | 0 | 100 | 2.5 |
| Detector: | 254 nm |
| Diluent: | 60:5:35 Acetonitrile:Tetrahydrofuran:water |

Example 1

Atorvastatin Epoxy Dihydroxy Synthesis

Atorvastatin calcium salt (1.0 g) was dissolved in a mixture of acetonitrile-water (1200 ml-800 ml) and methylene blue (1 mg) was added to the solution. The solution was stirred in an open flask at ambient temperature, and irradiated with visible light (tungsten lamp, 100 W, distance 10 cm) for 2 hours. Acetonitrile was evaporated under vacuum, and precipitated solid was filtered giving, after drying, a crude product (0.5 g) containing impurities at 32 and 33 min. (HPLC control)

The crude product (3.6 g) was purified by column chromatography on silica gel with dichloromethane as eluent, giving the mixture of the impurities at 32 and 33 min (1.6 g). The product was dissolved in dichloromethane (15 ml). The solution was stirred at ambient temperature while a solid was precipitated within a few minutes. The solid was filtered giving, after drying, the product (80 mg).

Example 2

Crystallization of Form VIII

Atorvastatin hemi-calcium salt form V (5 g) was added to a boiling solution of ethanol 96% (150 ml) to obtain a solution. The solution was refluxed for 2 hours (during that time atorvastatin hemi-calcium salt was recrystallized), then cooled to 20° C. during 1.5 hours and stirred at this temperature for an additional 16 hours. Filtration and drying in a vacuum oven at 40° C. for 24 hours and then at 60° C. for 24 hours gave atorvastatin hemi-calcium salt form VIII.

Example 3

Crystallization of the Forms of Atorvastatin Calcium

Modifying the process in Example 2 by changing the medium of crystallization results in the following crystal forms:

| Crystal form | Medium of crystallization |
|---|---|
| Amorphous | Ethyl acetate/n-Hexane (Esters/aliphatic or cyclic or branched Hydrocarbons) |
| Amorphous | Acetone |
| | Acetonitrile |
| Amorphous | THF/Toluene |
| Form I | traces of MTBE/MeOH/water |
| Form II | MeOH/water |
| Form IV | 1-Butanol |
| | EtOH/water |
| | MeOH |
| Form V | EtOH/water |
| Form VI | Acetone/water |
| Form VII | EtOH |
| Form VIII | EtOH, MeOH/water |
| | EtOH |
| | 1-Butanol/water |
| | IPA/water |
| Form IX | 1-Butanol |
| | 1-Butanol/n-Hexane |
| | 1-Butanol/IPA |
| | 1-Butanol/water |
| | EtOH |
| | 1-Butanol/EtOH |
| Form X | EtOH/water |
| Form XI | MEK |
| | IPA |
| Form XII | EtOH/water |

What is claimed is:

1. Isolated atorvastatin epoxy dihydroxy (AED), having the formula:

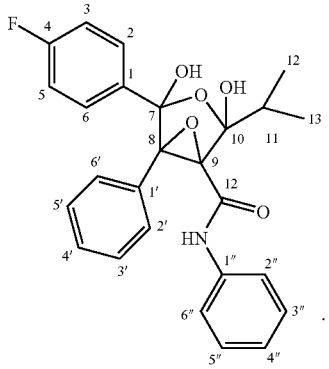

* * * * *